Dec. 23, 1969 H. C. SWIM Plant Pat. 2,957
OLIVE TREE
Filed April 2, 1968
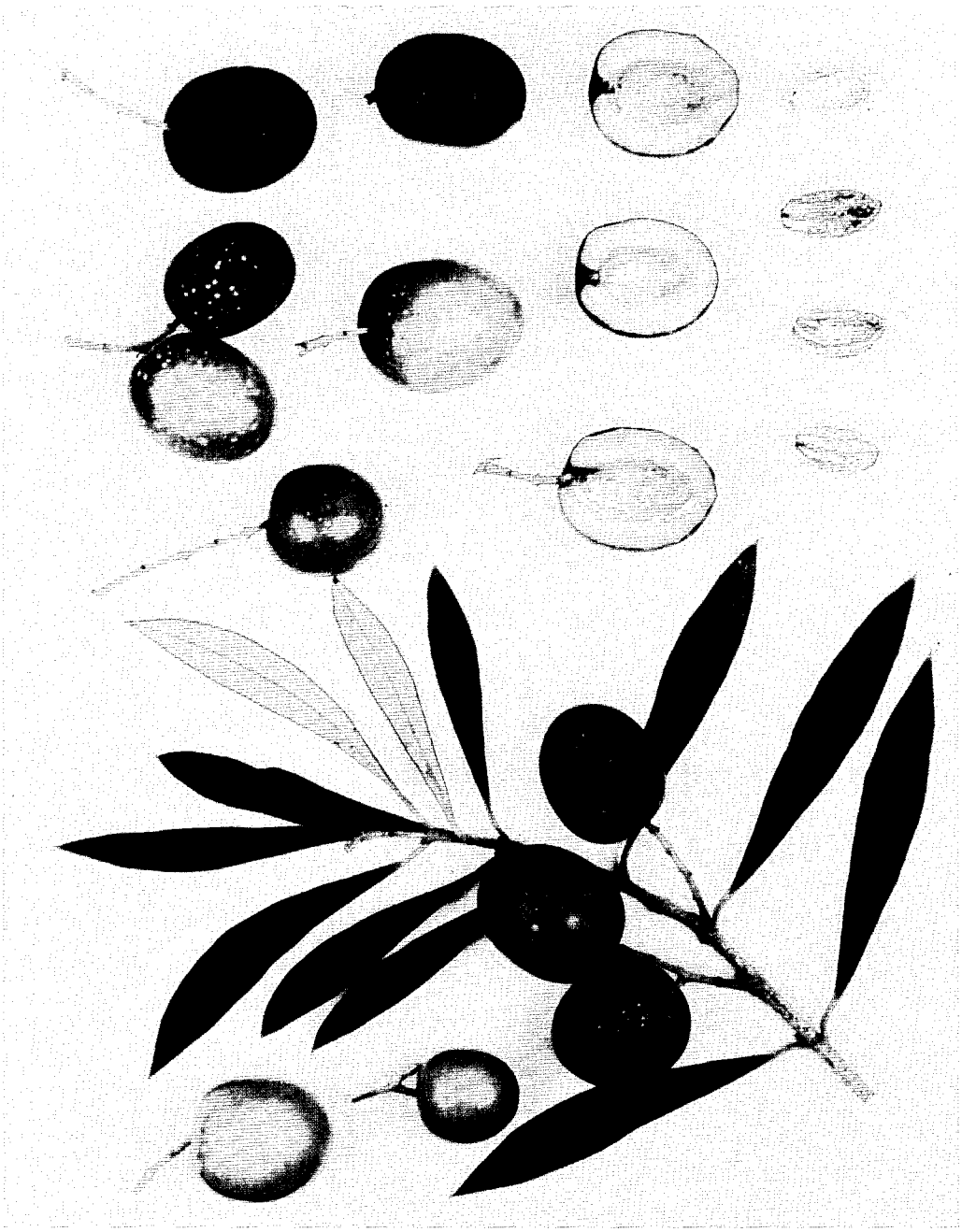
Inventor.
H. C. Swim
By: Robb & Robb
Attorneys

United States Patent Office

Plant Pat. 2,957
Patented Dec. 23, 1969

2,957
OLIVE TREE

Herbert C. Swim, Ontario, Calif., assignor to Armstrong Nurseries, Inc., Ontario, Calif., a corporation of California

Filed Apr. 2, 1968, Ser. No. 718,269
Int. Cl. A01h *5/08*
U.S. Cl. Plt.—33 1 Claim

The present invention relates to a new and distinct variety of olive tree which was originated by me as a selected open-pollinated seedling of the olive variety known as "Ascolano" (unpatented) and resulting from seedlings from fruit that fell to the ground from the parent tree which was being grown under my direction and supervision on the nursery property of my assignee situated at Ontario, Calif., said seedlings having germinated through natural means and then having been transplanted by me for study, test, selection, evaluation and final development.

The objective of my efforts aforesaid was to produce a new and improved olive variety having the desirable commercial qualities of the varieties "Ascolano" and "Manzanillo" (unpatented) which was growing adjacent to the "Ascolano" female parent.

This objective was not fully achieved, but other desirable features, as evidenced by the following unique combination of characteristics which are outstanding in the new variety and which distinguish it from its parents, as well as from all other olive varieties of which I am aware are:

(1) An extremely vigorous tree habit;

(2) A spreading habit of growth most nearly similar to that of the variety "Manzanillo," but in general, being even more spreading than that variety;

(3) A leaf shape most typical of that of the variety "Sevillano" (unpatented) than any other of which I am aware, but being distinguished as to shape from "Sevillano" leaves by being characteristically more slenderly cuneate at the base and averaging greater in length, while the margins are characteristically flat instead of being rolled downward like the leaf margins of "Sevillano" and most other olive varieties known to me;

(4) A characteristic yellow-green color on the under surface of the leaves instead of a more silvery-green or gray-green color typical of most other varieties known to me;

(5) A regular flowering habit, with high pollen viability which make the new variety a suitable pollenizer for other commercial olive varieties and particularly for the "Manzanillo" variety;

(6) A tendency toward heavy fruit production, with at least some flowers and attendant fruit being produced each season under normal orchard conditions and with the consequent ability of the new variety to cross-pollinate "Manzanillo" flowers with its highly viable pollen which is particularly compatible with the flowers of "Manzanillo;"

(7) A habit of bearing fruit both singly and two to a stem;

(8) A considerable variation of the size and shape of the fruit, but generally being of medium size and most nearly resembling that of "Manzanillo" fruit in size, but being more characteristic of the shape and lenticel markings of "Ascolano" fruit, with the lenticels being relatively inconspicuous at the beginning of ripening and becoming more prominent as ripening progresses; and (9) A quite rich fruit flavor when pickled, but with the objectionable tenderness of the "Ascolano" variety, and combined with the relatively small fruit size in comparison with the "Ascolano" variety, making it inferior to the "Manzanillo" fruit for pickling use.

The "Ascolano" variety is more erect and more compact than the new variety in respect to its tree habit, but is less vigorous than the new variety; the leaves of "Ascolano" are dark green in color and are comparatively broad and long, giving the tree a well-clothed appearance; while the flowers of "Ascolano" are considered a reasonably good pollenizer for the variety "Manzanillo," they are not as effective in this respect as the flowers of the new variety; and the lentcels on the wood of "Ascolano" at all stages are relatively small in number and size and are characteristically round in shape or nearly so.

As compared with the variety "Ascolano" and others most comparable to the new variety, the new variety has a more vigorous and more spreading tree habit; the flowers of the new variety have the ability to more effectively pollinate those of "Manzanillo;" the fruit of the new variety is substantially smaller in size than that of "Ascolano;" and the new variety has a more consistent flower production than "Ascolano." To the best of my knowledge, the tree of the new variety is the most vigorous olive tree in commerce and is most closely approached in this respect by its sibling variety known as "Bonita" (unpatented) from which the new variety may be easily distinguished by a more upright and compact tree habit of "Bonita" which bears relatively smaller crops of flowers and fruit, and has a distinctly different shape, size and color of the leaves. The conspicuous, characteristically greenish-yellow color on the under surface of the leaves of the new variety further distinguishes the new variety from all other olive varieties known to me, as well as the large number and elliptical shape of the large and prominent lenticels which are quite distinctive in the new variety.

Asexual reproduction of my new variety, as performed by me by cuttings at Ontario, Calif., shows that the foregoing characteristics and distinctions come true to form and are established and transmitted through succeeding propagations.

The accompanying drawing shows typical specimens of the foliage, stems, fruit and pits of my new variety in various stages of development, with both exterior and sectional views of the fruit being shown, all as depicted in color as nearly true as it is reasonably possible to make the same in a color illustration of this character.

The following is a detailed description of my new olive variety, as based upon observations of specimens grown at Ontario, Calif., with color terminology in accordance with Robert F. Wilson's Horticultural Colour Chart (hereinafter abbreviated as (W)) and Ridgway's Color Standards and Nomenclature (hereinafter abbreviated as (R)), except where general color terms of ordinary distionary significance are obvious:

TREE

Habit: Very vigorous; somewhat more spreading than the parent variety "Ascolano" and a great deal more spreading than the common varieties of olive in commerce, except perhaps the "Manzanillo" variety.

Fruit production: The original tree, after reaching maturity, produced a quite regular crop as long as it was given normal commercial orchard treatment, and trees that were asexual reproductions thereof have consistently borne heavy fruit crops at Hemet, Calif., where they were given normal commercial olive orchard care.

Current growth:

*Surface texture.*—Smooth at first, but the lenticels become unusually prominent, larger and elliptical in shape much more rapidly than in any other variety known to me.

*Color.*—Near Lettuce Green, Plate V (R), but as the growth ages, it is influenced more strongly by the prominent and numerous lenticels which have a corky appearance, and also as the growth ages, the surface acquires a bloom of a silvery appearance and the lenticels become somewhat grayed.

Two-year wood:

*Surface texture.*—At this stage, the bloom or silvery surface has become more pronounced and a fissuring or cracking of the bark begins to take place, and the lenticels become more prominent, more enlarged, and now begin to become particularly distinctive in the new variety.

*Color.*—The general color of the bark, excluding the lenticels, appears near Pale Cendre Green, Plate VI (R).

Old wood:

*Surface texture.*—Quite roughened due to the enlargement of the very prominent lenticels which give the bark a quite rough appearance, and the fissuring and cracking is no longer apparent.

*Color.*—Basic color is near Olive Green, Plate IV (R), but is overlaid and affected by both the silvering or bloom on the surface, as well as the very numerous lenticels which are now enlarged and grayed in appearance.

Leaves:

*Size.*—When mature, leaves usually range from 2 inches to 3 inches long and from 3/8 inch to 9/16 inch wide.

*Shape.*—Linear-lanceolate; apex tapered but acute; base slenderly cuneate; generally quite flat; only rarely with margins rolled downward very slightly; very rarely are the leaves twisted as is so typical of the sister variety "Bonita."

*Color (mature).* — Upper surface — near Cossack Green, Plate VI (R). Under surface—near Oural Green, Plate XVIII (R), but approaching Pale Dull Green-Yellow, Plate XVII (R).

*Color (immature).*—Upper surface—near Light Bice Green, Plate XVII (R). Under surfrace—between Oural Green, Plate XVII (R) and Light Lumiere Green, Plate XVII (R).

*Petiole.*—From 3/16 inch to 5/16 inch long; somewhat smaller caliper than in the varieties "Manzanillo," "Sevillano" and "Bonita."

*Margin.*—Typically entire; unusually flat and rarely with a very slightly rolled margin.

Vegetative buds:

*Size.*—Medium.

*Shape.*—Usually on a stalk and covered by twin brownish bracts.

*Bracts.*—Covered by a short pubescence or brownish bloom which disappears when growth begins.

FLOWERS

Clusters: Somewhat more compact than is typical of other varieties known in commerce, and flowers tend to open at about the same time as the flowers of the parent variety "Ascolano."

Pollen: Noticeably profuse in quantity.

Pistils: Usually well developed and not typical on a consistent basis of many varieties known in commerce in southern California.

FRUIT

Ripening date: Fruit usually ripens at about the same time as the fruit of "Manzanillo" or possibly a lattle later, usually in early to mid-November, depending on the amount of the crop; the heavier the crop, the later the maturation usually results.

Color: At first between Pea Green, Plate 61/1, page 61 (W) and Pod Green, Plate 061/1, page 120 (W) while unripe, becoming near Magnolia Purple, Plate 030/2, page 114 (W) to Magnolia Purple, Plate 030, page 114 (W), and then darkening to near Maroon, Plate 1030/3, page 185 (W) through Maroon, Plate 1030, page 185 (W).

Size:

*Length.*—From 7/8 inch to 1 1/16 inches.

*Width.*—From 3/4 inch to 1 1/16 inch.

Stem cavity:

*Width.*—1/8 inch.

*Depth.*—1/16 inch.

Form: Fruit varies from oblong or elliptical to occasionally heart-shaped.

Borne: Either 1 or 2 per stem.

Apex: The stigma is persistent in about half of the fruits, but usually the apex otherwise is rounded in the more perfectly formed fruits, and sometimes is evident in imperfectly formed fruits as a slightly raised tip or apex.

Stem: Moderately short in length and moderately sturdy in caliper.

Skin:

*Lenticels.*—Conspicuous lenticels are typically like those of "Ascolano," but are somewhat inconspicuous in the early stages of development and become increasingly conspicuous as coloration develops.

*Texture.*—Tender like the skin of "Ascolano" fruit, but not as extreme as the latter.

Pit:

*Size.*—Length—from 9/16 inch to 5/8 inch. Width—from 1/4 inch to 5/16 inch.

*Shape.*—Usually somewhat reniform and often with a sharp point.

*Surface.*—Rough and typified by rather prominent alternating ridges and furrows running longitudinally, but somewhat more obscure at the base, with two main furrows forming the halves of the endocarp and being prominent and continuous from base to apex.

*Base.*—Usually slightly oblique.

*Apex.*—Usually acute and sharp, but sometimes oblique.

*Color.*—From near Pinkish-Buff, Plate XXIX (R) to some areas of seed stained with Warm Sepia, Plate XXIX (R).

Flesh:

*Texture.*—Tending to tenderness like the parent variety "Ascolano."

*Color.*—Between near white and Ivory Yellow, Plate XXX (R), when ripe.

Pickling quality: Richly flavored when pickled with the home or green-ripe process, and being substantially richer in flavor than the variety "Ascolano;" sometimes the flavor is sufficiently strong as to be objectionable to some tastes.

I claim:

1. A new and distinct variety of olive tree, substantially as herein shown and described, characterized particularly as to novelty by the unique combination of an extremely vigorous tree habit, a spreading habit of growth most nearly similar to that of the variety "Manzanillo," but in general, being even more spreading than that variety, a leaf shape most typical of that of the variety "Sevillano" (unpatented) than any other of which I am aware, but being distinguished as to shape from "Sevillano" leaves by being characteristically more slenderly cuneate at the base and averaging greater in length, while the margins are characteristically flat instead of being rolled downward like the leaf margins of "Sevillano" and most other olive varieties known to me, a characteristic yellow-green color on the under surface of the leaves instead of a more silvery-green or gray-green color typical of most other varieties known to me, a regular flowering habit, with high pollen viability which make the new variety a suitable pollenizer for other commercial olive varieties, and particularly for the "Manzanillo" variety, a tendency toward heavy fruit production, with at least some flowers and attendant fruit being produced each season under normal orchard conditions and with the consequent ability of the new variety to cross-pollinate "Manzanillo" flowers with its highly viable pollen which is particularly compatible with the flowers of "Manzanillo," a habit of bearing fruit both singly and two to a stem, a considerable variation of the size and shape of the fruit, but generally being of medium size and most nearly resembling that of "Manzanillo" fruit in size, but being more characteristic of the shape and lenticel markings of "Ascolano" fruit, with the lenticels being relatively inconspicuous at the beginning of ripening and becoming more prominent as ripening progresses, and a quite rich fruit flavor when pickled, but with the objectionable tenderness of the "Ascolano" variety, and combined with the relatively small fruit size in comparison with the "Ascolano" variety, making it inferior to the "Manzanillo" fruit for pickling use.

No references cited.

ROBERT E. BAGWILL, Primary Examiner